United States Patent [19]

Nakayama et al.

[11] 4,190,589
[45] Feb. 26, 1980

[54] CORIOLIN DERIVATIVES AND PROCESS FOR PRODUCING THE SAME

[75] Inventors: Yuya Nakayama, Omiya; Mamoru Kunishima, Tokorozawa; Akira Matsuda, Omiya; Tomio Takeuchi; Hamao Umezawa, both of Tokyo, all of Japan

[73] Assignee: Nippon Kayaku Kabushiki Kaisha, Tokyo, Japan

[21] Appl. No.: 902,824

[22] Filed: May 4, 1978

[30] Foreign Application Priority Data

May 17, 1977 [JP] Japan .................................. 53/56019

[51] Int. Cl.² ............................................ C07D 493/10
[52] U.S. Cl. .................................. 260/343.6; 424/279
[58] Field of Search ...................................... 260/343.6

*Primary Examiner*—Norma S. Milestone
*Attorney, Agent, or Firm*—Russell & Nields

[57] ABSTRACT

Coriolin derivatives having antitumor activity and low toxicity represented by the following general formula:

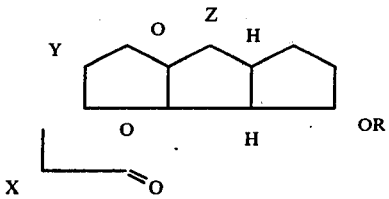

where
R: $-CO(CH_2)_6CH_3$ or $-COCH(OH)(CH_2)_5CH_3$,
X: $=CH_2$ or $-COOR'$,
R': H or lower alkyl group.
Y: OH or $=O$ and
Z: $-OH$ or $OCH_3$, as well as the process for producing the above derivatives are disclosed.

5 Claims, No Drawings

CORIOLIN DERIVATIVES AND PROCESS FOR PRODUCING THE SAME

DETAILED DESCRIPTION OF THE INVENTION

Coriolin, coriolin B and coriolin C are natural terpenoid compounds that have been extracted and isolated from culture solution of *Basidiomycetes Coriolus* consors by Umezawa, et al (refer to J. Antibiotics 24, 631 (1971), 22, 215 (1969), and Tetrahedron Letters 1971, 1955). Coriolin compounds having antitumor activity known so far include, in addition to the above coriolin and coriolin C, such derivatives as 5-dehydrocoriolin B, 5,8-dehydrocoriolin B and the like (refer to the above J. Antibiotics and Tetrahedron Letters).

This invention relates to coriolin derivatives represented by the general formula:

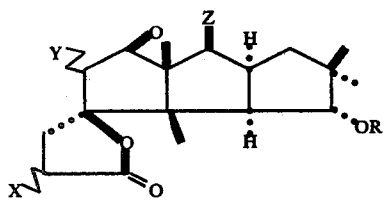

(I)

where

R: —$CO(CH_2)_6CH_3$ or —$COCH(OH)(CH_2)_5CH_3$,
X: =$CH_2$ or —COOR',
R': H or lower alkyl group,
Y: —OH or =O and
Z: —OH or —$OCH_3$, as well as the process for producing the above derivatives.

The compound (I) of this invention has such a modified chemical structure that the epoxide group at $C_4$-position in the foregoing coriolin compounds is replaced with an α-substituted 5-membered lactone structure and shows an effect of prolonging survival period in mouce leukemia L-1210. Further, since this compound exhibits a higher inhibitive activity than known coriolin compounds against experimental tumor cells such as Hela cells and yet has only a comparatively low toxicity, it can be expected to apply the compound to the remedy of man's tumor.

Typical examples of the compound (I) of this invention include those represented by the following general formula:

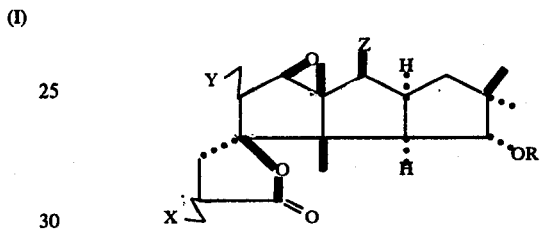

| Compound No. | R | X | Y | Z | Compound | Appearance mp °C | Molecular formula Calculated % / Experimental % (C) Calculated % / Experimental % (H) | Infrared Absorption Spectrum cm$^{-1}$ (KBr method) | | | | |
|---|---|---|---|---|---|---|---|---|---|---|---|---|
| 1 | —CO(CH$_2$)$_6$CH$_3$ | =CH$_2$ | —OH | —OCH$_3$ | 1α-octanoyl-4-(16-methyl-ene-15α-butanolid)-5β-hydroxy-6β,7β-oxide-8β-methoxyhirstan | Crystal 152~153 | C$_{26}$H$_{40}$O$_7$ 67.21 / 67.39 8.68 / 8.55 | 3405 1312 1042 811 | 2925 1265 1010 751 | 1739 1200 980 721 | 1664 1165 931 672 | 1465 1108 899 |
| 2 | —CO(CH$_2$)$_6$CH$_3$ | =CH$_2$ | —OH | —OH | 1α-octanoyl-4-(16-methyl-ene-15α-butanolid)-6β,7β-oxide-5β,8β-dihydroxyhirstan | Crystal 164.5~165.5 | C$_{25}$H$_{38}$O$_7$ 66.64 / 66.70 8.50 / 8.47 | 3420 1468 1132 932 810 | 2940 1390 1097 900 750 | 1771 1269 1067 888 726 | 1733 1190 1013 864 670 | 1669 1167 961 842 |
| 3 | —COCH(CH$_2$)$_5$CH$_3$ \| OH | =CH$_2$ | —OH | —OCH$_3$ | 1α-(α-hydroxyoctanoyl)-4-(16-methylene-15α-butanolid)-5β,-hydroxy-6β,7β-oxide-8β-methoxyhirstan | Amorphous powder 54~58 | C$_{26}$H$_{40}$O$_8$ 64.98 / 65.35 8.39 / 8.26 | 3440 1462 1110 930 | 2950 1375 1085 810 | 1770 1300 1040 750 | 1740 1269 1010 720 | 1664 1200 952 670 |
| 4 | —COCH(CH$_2$)$_5$CH$_3$ \| OH | =CH$_2$ | —OH | —OH | 1α-(α-hydroxyoctanoyl)-4-(16-methylene-15α-butanolid)-6β,7β-oxide-5β,8β-dihydroxyhirstan | Crystal 129~131 | C$_{25}$H$_{38}$O$_8$ 64.36 / 64.25 8.21 / 8.20 | 3430 1465 1133 935 | 2950 1380 1100 810 | 1775 1275 1070 755 | 1730 1200 1015 720 | 1670 1175 980 690 |
| 5 | —CO(CH$_2$)$_6$CH$_3$ | =CH$_2$ | =O | —OCH$_3$ | 1α-octanoyl-4-(16-methyl-ene-15α-butanolid)-5-oxo-6β,7β-oxide-8β-methoxyhirstan | Crystal 68~69 | C$_{26}$H$_{38}$O$_7$ 67.51 / 67.38 8.28 / 8.30 | 3440 1467 1270 1100 960 810 | 2950 1405 1228 1079 933 779 | 2680 1370 1210 1042 920 760 | 1750 1342 1160 1020 892 723 | 1669 1288 1117 1010 855 692 835 669 |
| 6 | —CO(CH$_2$)$_6$CH$_3$ | =CH$_2$ | =O | —OH | 1α-octanoyl-4-(16-methyl-ene-15α-butanolid)-5-oxo-6β,7β-oxide-8β-hydroxy-hirstan | Crystal 175~175.5 | C$_{25}$H$_{36}$O$_7$ 66.94 / 67.00 8.09 / 8.06 | 3410 1655 1290 1083 931 748 | 3300 1452 1265 1022 889 712 | 2910 1390 1232 1002 872 680 | 2840 1369 1189 960 839 | 1727 1332 1159 948 800 |
| 7 | —COCH(CH$_2$)$_5$CH$_3$ \| OH | =CH$_2$ | =O | —OCH$_2$ | 1α-(α-hydroxyoctanoyl)-4-(16-methylene-15α-butanolid)-5-oxo-6β,7β-oxide-8β-methoxyhirstan | Amorphous powder 42~45 | C$_{26}$H$_{38}$O$_8$ 65.25 / 64.96 8.00 / 8.21 | 3490 1378 1002 851 659 | 2940 1279 959 803 | 1760 1181 930 769 | 1662 1110 910 720 | 1463 1040 890 681 |

-continued

| Compound No. | R | X | Y | Z | Compound | Appearance mp °C. | Molecular formula Calculated % Experimental % C | Calculated % Experimental % H | Infrared Absorption Spectrum cm⁻¹ (KBr method) | | | | |
|---|---|---|---|---|---|---|---|---|---|---|---|---|---|
| 8 | —COCH(CH₂)₅CH₃<br>       |<br>      OH | =CH₂ | =O | —OH | 1α-(α-hydroxyoctanoyl)-4-(16-methylene-15α-butanolid)-5-oxo-6β,7β-oxide-8β-hydroxyhirstan | Crystal 98 ~ 99 | C₂₅H₃₆O₈<br>64.63<br>64.42 | 7.81<br>7.76 | 3410<br>1665<br>1290<br>1070<br>890<br>690 | 3350<br>1450<br>1270<br>1020<br>850<br>660 | 2930<br>1390<br>1230<br>1000<br>800 | 2845<br>1370<br>1190<br>960<br>765 | 1730<br>1330<br>1160<br>950<br>715 |
| 9 | —CO(CH₂)₆CH₃ | —COOC₂H₅ | =O | —OCH₃ | 1α-octanoyl-4-(16-carboethoxy-15α-butanolid)-5-oxo-6β,7β-oxide-8β-methoxyhirstan | Crystal 129 ~ 130.5 | C₂₉H₄₂O₉<br>65.05<br>65.00 | 8.10<br>8.12 | 3480<br>1375<br>1160<br>895<br>722 | 2950<br>1345<br>1118<br>863<br>655 | 1795<br>1300<br>1010<br>842 | 1740<br>1269<br>968<br>778 | 1463<br>1220<br>932<br>741 |
| 10 | —COCH(CH₂)₅CH₃<br>       |<br>      OH | —COOC₂H₅ | =O | —OCH₃ | 1α-(α-hydroxyoctanoyl)-4-(16-carboethoxy-15α-butanolid)-5-oxo-6β,7β-oxide-8β-methoxyhirstan | Crystal 138 ~ 139 | C₂₉H₄₂O₁₀<br>63.25<br>63.21 | 7.69<br>7.85 | 3485<br>1375<br>1165<br>900<br>725 | 2960<br>1345<br>1120<br>875<br>655 | 1800<br>1300<br>1000<br>850 | 1740<br>1270<br>970<br>780 | 1470<br>1220<br>932<br>740 |
| 11 | —CO(CH₂)₆CH₃ | —COOH | =O | —OCH₃ | 1α-octanoyl-4-(16-carboxy-15α-butanolid)-5-oxo-6β,7β-oxide-8β-methoxyhirstan | Amorphous powder 40 ~ 45 | C₂₇H₃₈O₉<br>64.01<br>64.22 | 7.56<br>7.49 | 3440<br>1598<br>1110<br>934 | 2950<br>1465<br>1055<br>890 | 2880<br>1418<br>1019<br>837 | 1795<br>1380<br>985<br>775 | 1745<br>1165<br>965<br>723 |
| 12 | —CO(CH₂)₆CH₃ | —COOCH₃ | =O | —OCH₃ | 1α-octanoyl-4-(16-carbomethoxy-15α-butanolid)-5-oxo-6β,7β-oxide-8β-methoxyhirstan | Crystal 107 ~ 109 | C₂₈H₄₀O₉<br>64.59<br>64.32 | 7.74<br>7.80 | 3440<br>1451<br>1300<br>1118<br>960<br>796 | 2940<br>1439<br>1242<br>1098<br>931<br>772 | 1787<br>1380<br>1220<br>1048<br>910<br>750 | 1758<br>1350<br>1185<br>1018<br>890<br>740 | 1733<br>1310<br>1147<br>990<br>840<br>668 |

The compound (I) of this invention can be produced in the processes A or B each represented by the reaction schemes shown below:

Process A

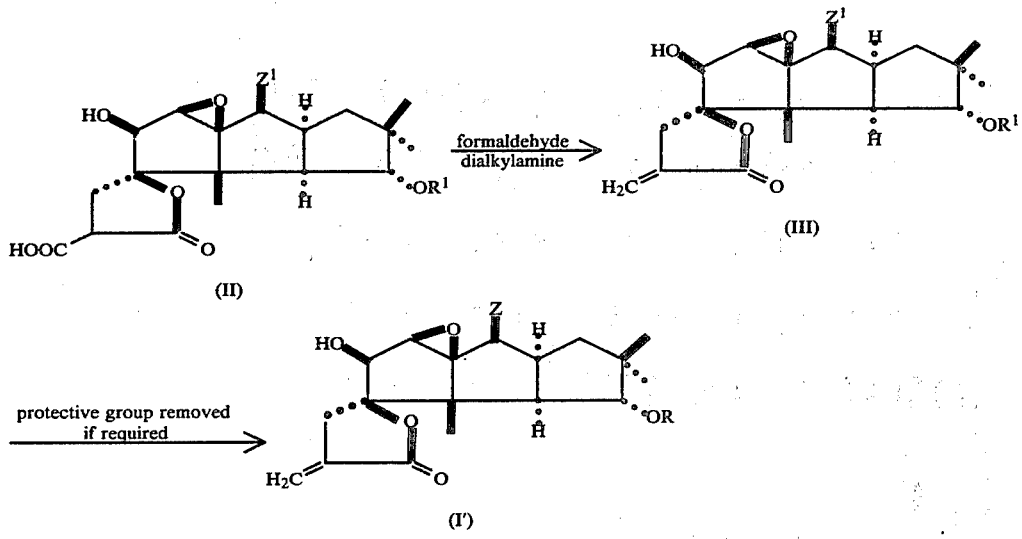

where $R^1$: —CO(CH$_2$)$_6$CH$_3$, —COCH(OH)(CH$_2$)$_5$CH$_3$, $$-\underset{\underset{\text{O-protective group}}{|}}{\text{COCH}}(\text{CH}_2)_5\text{CH}_3$$

$Z^1$: —OCH$_3$, —OH, O-protective group
R: CO(CH$_2$)$_6$CH$_3$, —COCH(OH)(CH$_2$)$_5$CH$_3$
Z: —OH, —OCH$_3$ Process B

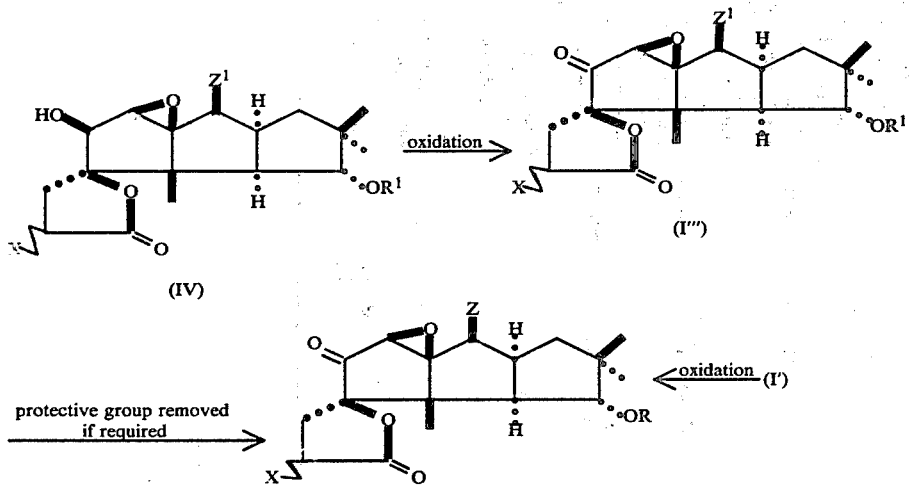

where $R^1$, $Z^1$, R and Z have the same meanings as above, and X: =CH$_2$, —COOH, —COO-lower alkyl.

In the process A, the compound (I′) of the compound (I) can be produced by reacting dialkylamine and formaldehyde with the compound (II) in a solvent and removing protective groups if any. More specifically, 1 mol of the compound (II) is dissolved in 2–10 times by volume of inactive solvent, preferably a lower alcohol such as ethanol, to which solution is added dialkylamine such as diethylamine in an amount between 1.5–8 times, preferably, 3–5 times in molar ratio and aqueous formaldehyde in an amount between 1.5–6 times, preferably, 2–4 times in molar ratio and they are reacted at 5°–50° C., preferably, 15°–30° C. for 2–8 hours, preferably, 3–5 hours. After the completion of the reaction, the reaction solution is extracted, either as it is or after removal of protective groups if present by addition of concentrated hydrochloric acid followed by dilution with water, with water immiscible volatile solvent such as chloroform, and the extract is concentrated to dryness under vacuum. The resulted residues are treated with a volatile hydrocarbon (petrolic) such as n-hexane and the cystal of the aimed products can be obtained. Where the aimed products of high purity can not be obtained or they are resulted only at low yield by the above procedures, the extract from the reaction solution or the mother solution separated the crystal is isolated and purified by a method using an adsorbent such as a chromatographic process and then crystallied whereby the purified products can be obtained at high yield.

In the process B, the compound (I″) can be produced by oxidizing the compound (I′), its derivatives or the compound (IV) which may contain protective groups in an organic solvent. In the case employing the compound (IV), the oxidizing process is followed by removing of protective groups in intermediate (I‴), if required.

In this oxidizing process, preferred reacting medium includes pyridine, benzene, acetone, acetic acid, dimethylsulfoxide or the mixture of them.

Preferred oxidizing agent includes chromic acid, dicyclohexylcarbodiimide and the like, chromic acid being particularly desired.

The amount of the oxidizing agent used is between 1–10, preferably, 3–7 times in molar ratio per mol of the starting compound.

The aimed compound (I) can be obtained from the reaction solution by filtrating the reaction solution, extracting the filtrate with an organic solvent such as ethylacetate and chloroform with addition of water, concentrating and drying the extract and then purifying the same through re-crystallization or silica chromatography.

Antitumor and antibiotic effects of the compound (I) of this invention are to be described.

1. Tumor Inhibition Test (1) Effect on Hela $S_3$ Cells

Hela $S_3$ cells were placed in a plastic schale at $0.7 \times 10^5$ cells/plate. Eagle MEM medium containing 60 μg kanamycin/ml and 10% calf serum (manufactured by Nissui Seiyaku, K.K.) was used. On the second day after the inoculation, the culture medium was replaced with a new Eagle MEM in which the compound of this invention had been added in various concentrations as shown in Table 2. Number of the cells was $1.58 \times 10^5$ cells/plate. After three day's culture, the culture medium was eliminated, washed with a physiological saline solution and treated with 0.05% trypsin for about 15 minutes at room temperature, and the cells were then dispersed by pipetting. Number of the cells was measured by a counter. In comparison to the control with no addition of the compound, inhibition rate (%) was determined based on the following equation and $LD_{50}$ was calculated:

$$\text{Inhibition (\%)} = \left[1 - \frac{\left(\begin{array}{c}\text{number of cells}\\\text{after addition}\\\text{of compound}\end{array}\right) - \left(\begin{array}{c}\text{number of cells at}\\\text{the time of addi-}\\\text{tion of compound}\end{array}\right)}{\left(\begin{array}{c}\text{number of cells}\\\text{in control}\end{array}\right) - \left(\begin{array}{c}\text{number of cells at}\\\text{the time of addi-}\\\text{tion of compound}\end{array}\right)}\right] \times 100$$

(2) Effect on L-1210 (Lymphatic leukemia)

L-1210 Cell, $1 \times 10^5$, 0.05 ml, was intraperitoneally inoculated to BDF mice and a specified amount of the agent (as 0.5% aqueous CMC suspension) was applied once a day for 10 days starting 24 hours after the inoculation. The dosage was as shown in Table 3.

Observation was continued till the mice died and the rate of prolonging the survival period was calculated in accordance with the following equation in comparison with control group (only 0.5% aqueous CMC solution was applied):

$$\text{Survival period prolonging rate} = \frac{\left(\begin{array}{c}\text{mean survival days for}\\\text{the tested group}\end{array}\right) - \left(\begin{array}{c}\text{means survival days}\\\text{for the control group}\end{array}\right)}{\text{Mean survival days for the control group}} \times 100$$

II Test Result

The effect for Hela $S_3$ cells and the effect of prolonging the survival period in L-1210 mice are shown in Table 2 and Table 3 respectively.

Table 2

| | Effect on Hela $S_3$ Cells | | |
|---|---|---|---|
| Compound No. | Concentration μg/ml | Inhibition rate (%) | LD μg/ml |
| 1 | 2 | 91.4 | 1.2 |
|   | 1 | 38.2 |   |
| 2 | 2 | 86.0 | 1.3 |
|   | 1 | 35.0 |   |
| 5 | 0.2 | 100 | 0.1 |
|   | 0.1 | 50.4 |   |
| 6 | 0.2 | 72.0 | 0.15 |
|   | 0.1 | 30.0 |   |
| 7 | 0.2 | 84.0 | 0.135 |
|   | 0.1 | 33.0 |   |
| 8 | 0.2 | 68.0 | 0.16 |
|   | 0.1 | 25.0 |   |
| 9 | 0.4 | 91.8 | 0.24 |
|   | 0.2 | 27.4 |   |
| 10 | 0.6 | 80.0 | 0.40 |
|    | 0.3 | 20.0 |   |
| 11 | 8 | 71.6 | 5.95 |
|    | 4 | 29.4 |   |
| 5-dehydro-coriolin B | 1 | 77.6 | 0.76 |
|    | 0.5 | 20.0 |   |

Table 3

| Effect of Prolonging Survival Period in L-1210 Mice | | | | | |
|---|---|---|---|---|---|
| Dosage g/mouse/days × 10 | 100 | 50 | 25 | 12.5 | 6 |
| Compound No. | | | | | |
| 1 | 120 | 110 | 110 | 100 | 100 |
| 2 | 123 | 132 | 110 | 105 | 105 |
| 5 | 169 | 160 | 148 | 141 | 106 |
| 6 | 175 | 165 | 145 | 145 | 125 |
| 7 | 175 | 160 | 142 | 136 | 125 |
| 8 | 178 | 157 | 149 | 120 | 105 |
| 9 | 141 | 134 | 113 | 106 | 99 |
| 10 | 146 | 136 | 120 | 110 | 110 |
| 11 | 148 | 141 | 148 | 134 | 106 |
| 5-dehydro-coriolin B | toxic | 144 | 137 | 138 | 106 |

Note:
The effect of prolonging the survival period was calculated based on the mean survival days as 100% for the control group with no application of the compound.

Test on Antibiotic Effect

Antibacterial effect of the compound (I) of this invention was measured based on minimum inhibitory concentration by way of agar streak method using buillon agar as culture medium. The results are shown in Table 4.

Table 4

| Minimum grow Inhibitory Concentration (mcg/ml) | | | |
|---|---|---|---|
| Micro-organisms Compound No. | Mycobacterium 607 | Staphlococus aures | Bacillus subtillis |
| 1 | 12.5 | 3.13 | 6.25 |

Table 4-continued

| Micro-organisms Compound No. | Minimum grow Inhibitory Concentration (mcg/ml) | | |
|---|---|---|---|
| | Mycobacterium 607 | Staphlococus aures | Bacillus subtillis |
| 2 | 12.5 | 6.25 | 6.25 |
| 5 | 12.5 | 25 | 3.13 |
| 6 | 25 | 25 | 3.13 |
| 7 | 12.5 | 25 | 3.13 |
| 8 | 25 | 25 | 6.25 |
| 9 | 25 | 50 | 6.25 |
| 10 | 50 | 50 | 12.5 |
| 11 | 100 | 100 | 25 |

As apparent from the foregoing results, the compound (I) of this invention showed an inhibitive activity at low concentration to Hela cells which are experimental tumor cells and the compound was comparable with known coriolin derivatives as controls regarding the effect for prolonging survival period for the mice inoculated with leukemia L-1210. Moreover, while the control coriolin derivatives showed toxicity at 100 μg/mouce, no toxicity was recognized at all for the compound (I) of this invention. An antibacterial effect were also recognized in the compound of (I) as well. Accordingly, application to antitumor agents and antibacterial agents can be expected for the compound (I) of this invention.

The starting compounds (II) and (III) used in this invention are produced from coriolin B which can be isolated at a high yield from the culture solution of basidiomycetes Corioulus consors (refer to U.S. Pat. No. 3,780,069 and from 5-dihydrocoriolin C (refer to U.S. Pat. No. 3,810,924) and by way of the following processes:

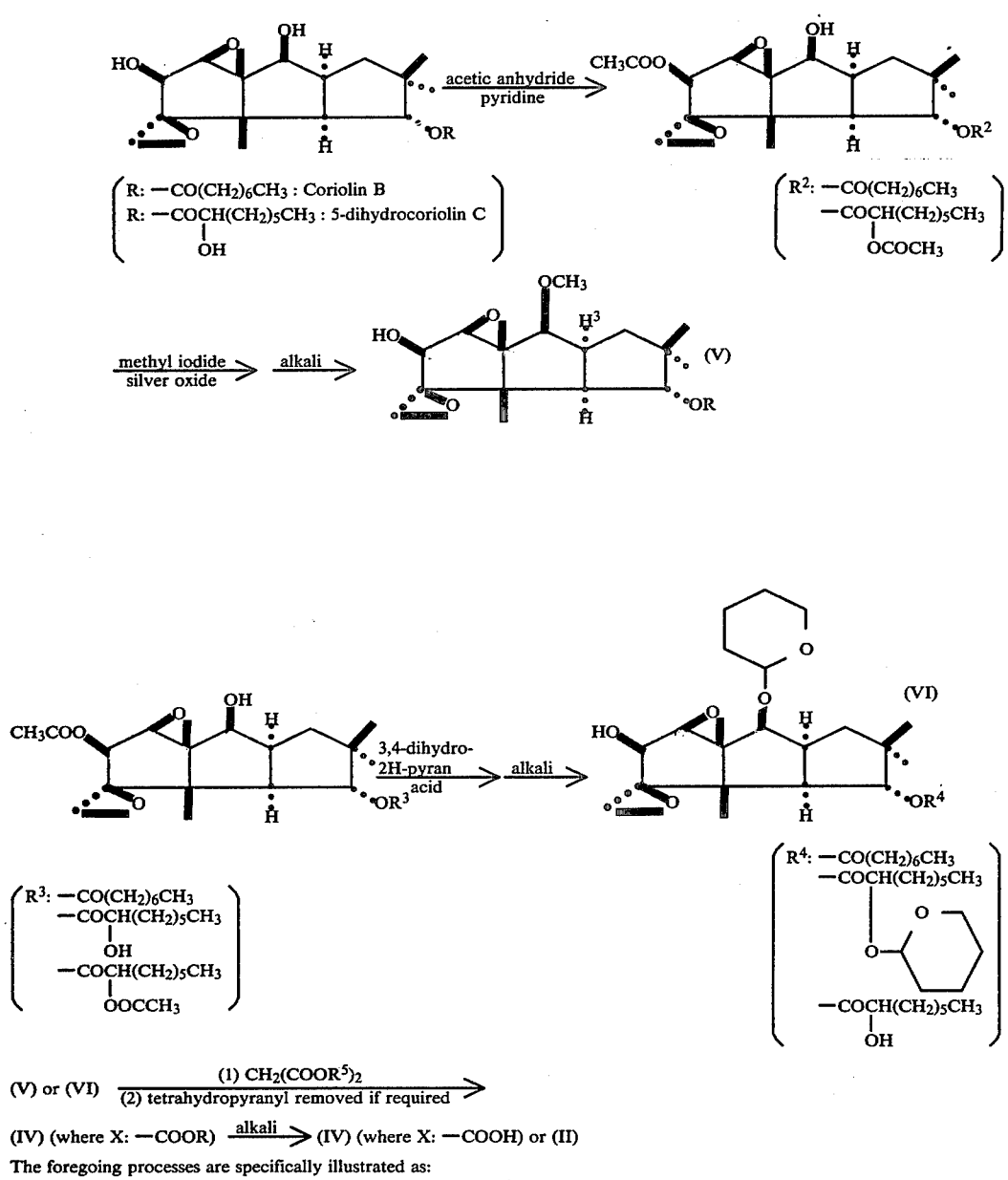

The foregoing processes are specifically illustrated as:

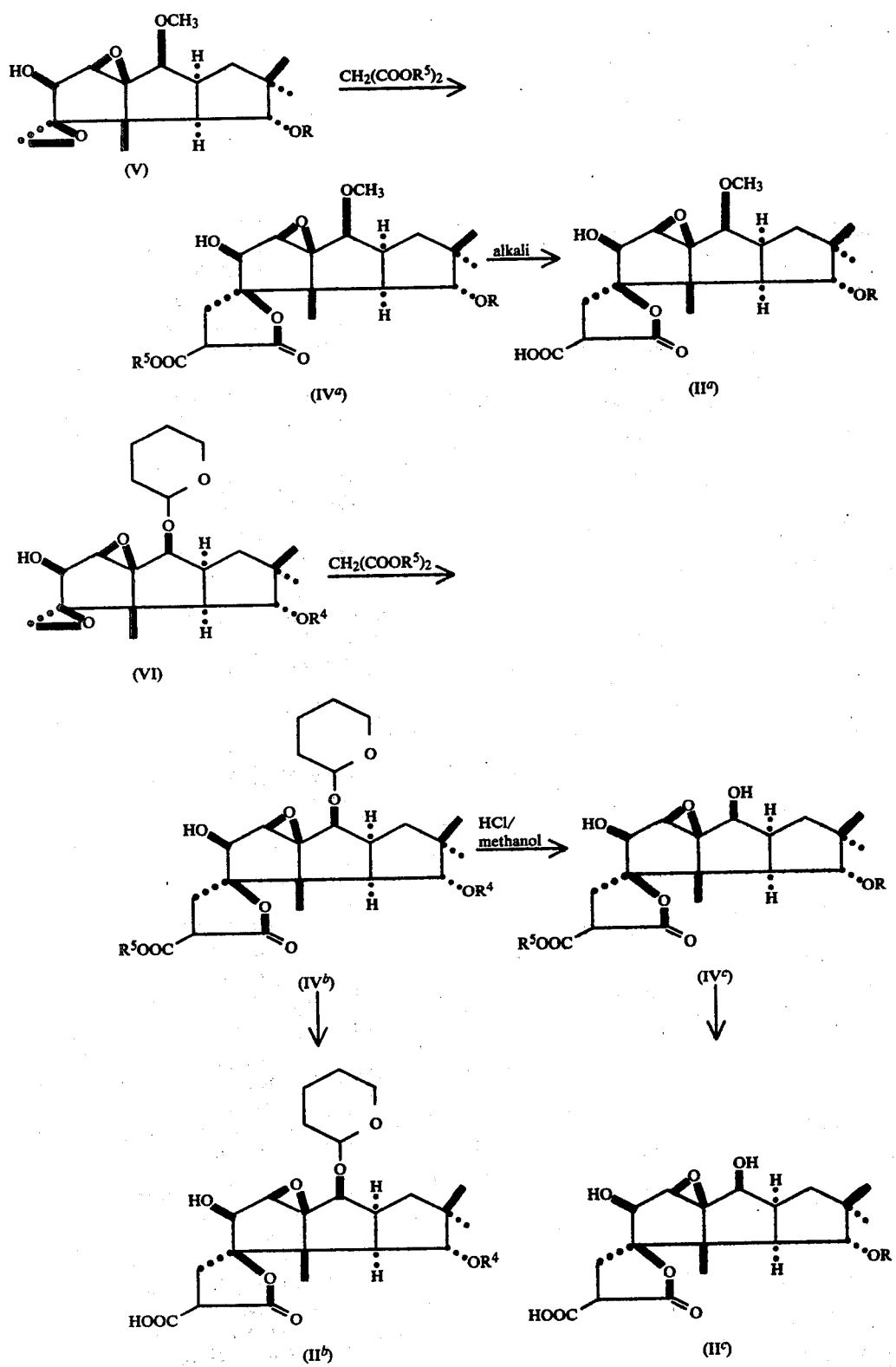
R: —CO(CH$_2$)$_6$CH$_3$,
—COCH(CH$_2$)$_5$CH$_3$,
    |
    OH
R$^5$: lower alkyl group
R$^4$: —CO(CH$_2$)$_6$CH$_3$,

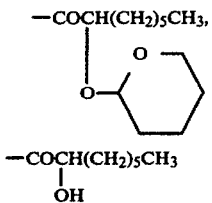

Process of producing starting compounds used in this invention is to be described by way of comparison examples.

COMPARISON EXAMPLE 1

Synthesis of 1α-octanoyl-4-(16-carboethoxy-15α-butanolid)-5β-hydroxy-6β,7β-oxide-8β-methoxyhirstan

(1) Synthesis of 5-acetylcoriolin B 3 g coriolin B was dissolved into a mixed solution of 15 ml pyridine and 1.05 ml acetic anhydride and left at 5° C. for two days. The reaction solution was pured to 100 ml water and precipitates were recovered through filtration, washed with water and then n-hexane successively and thereafter dried. The dried products were extracted in 20 ml methanol and the extract was concentrated, dried and recrystallized from acetone-water to obtain 1.75 g crude product.

The product was charged into a column filled with 85 ml silica gel and, after adsorption of the aimed products thereon, eluted by chloroform, recrystallized from acetone and water to obtain 1.6 g 5-acetyl coriolin in needle-like crystal. Melting point: 145° C. Yield: 46.5%.

(2) Synthesis of 8-methoxycoriolin B 1.5 g 5-acetylcoriolin B was dissolved in 3 ml dimethylformamide, to which were added 3.0 ml methyl iodide and 750 mg silver oxide under stirring and then further stirred for 4 hours at 40°–42° C. The reaction solution was filtered and the precipitates were washed with chloroform and joined to the filtrate. The solution was added with water of about five times in volume and then extracted with chloroform. The extracts were concentrated under vacuum, dried to solid. The residues were dissolved into a small amount of chloroform and poured into a column filled with 50 ml silica gel together with chloroform. Then, after adsorption on the columm, they were eluted by chloroform. Elute fraction containing 5-acetyl-8-methoxycoriolin B was collected, concentrated, dried to solid under vacuum and the residues were agitated together with n-hexane. Then, needle-like crystal of 5-acetyl-8-methoxycoriolin B was crystallized out and it was filtered and dried. Melting point: 115°–116° C. Yield: 79.7%.

650 mg of the 5-acetyl-8-methoxycoriolin B was dissolved in 65 ml methanol, to which was added 1.3 ml 2% aqueous solution of sodium hydrogen carbonate to perform reaction at 49°–52° C. for one hour and 40 minutes. The reaction solution was adjusted with its pH value to 5.0 using diluted hydrochloric acid and extracted with chloroform. The extracts were concentrated and dried under vacuum and recrystallied from a mixed solution of ethylacetate-n-hexane to obtain 550 mg 8-methoxycoriolin B in needle-like crystal. Melting point: 74.5°–75° C. Yield: 93.0%. NMR (CDCl$_3$)$^\delta$: 3.34 (—OC$\underline{H}_3$, s)

(3) Synthesis of 1α-octanoyl-4-(16-carboethoxy-15α-butanolid)-5β-hydroxy-6β,7β-oxide-8β-methoxyhirstan 473 mg metal sodium was dissolved in 9 ml absolute ethanol and 9 ml diethyl malonate was added thereto at a time while keeping the solution at 52° C. under stirring. After keeping the solution at the above temperature as it was for 30 minutes, 1.6 g 8-methoxycoriolin B was added at a time and dissolved therein under stirring and the solution temperature is kept for 50°–52° C. for further 8 hours.

To the above reaction solution, were added each 40 ml of ethylacetate and water, shaked in a separating funnel and left still to remove the aqueous layer, and the upper layer was neutralized with hydrochloric acid and washed with 20 m water.

The ethylacetate fraction layer was concentrated and dried to solid under vacuum, and the residues were stirred together with a small amount of n-hexane. The resulted crystal of the aimed products were filtered and dried to obtain 1.05 g needle-like crystal. Melting point: 152°–152.5° C. NMR(CDCl$_3$)$^\delta$: 3.26 (—OC$\underline{H}_3$, s) 4.29, 4.06 (—C$\underline{H}_2$CH$_3$, d, J=7)

Mother liquid for crystal was concentrated, dried and then subjected to chromatography using 45 ml silica gel in which it was eluted chloroform and then with 1% methanolchloroform. Fractions containing the aimed products were concentrated and dried to solid and the residues were treated with n-hexane to obtain 190 mg needle-like crystal. Melting point: 149°–151° C.

COMPARISON EXAMPLE 2

Synthesis of 1α-octanoyl-4-(16-carboethoxy-15α-butanolid)-6β,7β-oxide-5β,8β-dihydroxyhirstan

(1) Synthesis of 8-O-tetrahydropyranylcoriolin B 1.48 g 5-acetylcoriolin B was dissolved in 30 ml anhydrous benzene, to which were added 28 mg p-toluene sulfonic acid and 0.54 ml 3,4-dihydro-2H-pyran under stirring and left for 2 hours and 40 minutes at a room temperature. The reaction solution was twice washed with water with 10 ml water at each time to separate the benzene phase, which was concentrated and dried to solid under vacuum to obtain 2.1 g oily products of 5-acetyl-8-O-tetrahydropyranylcoriolin B. The above products were wholly dissolved in 140 ml methanol, and 2.8 ml 2% aqueous solution of sodium hydrogen carbonate was added thereto and kept for one hour and 20 minutes at 55°–60° C. The reaction solution was neutralized with hydrochloric acid and concentrated. The residues were dissolved in ethylacetate, washed with a small amount of water to isolate ethyl acetate phase, which was concentrated and dried under vacuum to obtain 1.68 g oily products of 8-O-tetrahydropyranylcoriolin B.

(2) Synthesis of 1α-octanoyl-4-(16-carboethoxy-15α-butanolid)-6β,7β-oxide-5β,8β-dihydroxyhirstan 433 mg metal sodium was dissolved in 9 ml absolute ethanol, to which 9 ml diethyl malonate was added and kept at 52°–63° C. for 30 minutes. Then, 1.68 g 8-0-tetrahydropyranylcoriolin B dissolved in 2.2 ml absolute ethanol was added. They were reacted at 54°–60° C. for 4 hours and 30 minutes and treated in the same manner as in the comparison example 1 (3) to extract aimed products and the solvent was distilled off from the extracts. 8.6 g of the residues were dissolved in 88 ml methanol, incorporated with 0.18 ml conc. hydrochloric acid, left at room temperature for one hour, neutralized with sodium hydroxide and then concentrated.

The residues were added with water and extracted with ethylacetate, and the extract was washed with water, concentrated, dried to solid and then treated with a small amount of n-hexane to crystallize the aimed products, which were recovered through filtration and dried to obtain 650 mg needle-like crystal. Melting point: 183°–186° C. Yield: 36.4%. NMR $(CDCl_3)^\delta$: 4.25, 4.03 ($OCH_2CH_3$, d, J=7).

COMPARISON EXAMPLE 3

Synthesis of 1α-(α-hydroxyoctanoyl)-4-(16-carboethoxy-15α-butanolid)-5β-hydroxy-6β,7β-oxide-8β-methoxyhirstan

(1) Synthesis of 2′,5-diacetyl-5-dihydrocoriolin C

In the same manner as in the comparison example 1 (1), 2 g 5-dihydrocoriolin C was acetylated using 10 ml pyridine and 1.4 ml acetic anhydride, subjected to silica gel chromatography and recrystallized to obtain 1.12 g 2′,5-diacetyl-5-dihydrocoriolin C in needle-like crystal. Melting point: 133.5° C. Yield: 47%.

(2) 5-dihydro-8-methoxycoriolin C 700 mg 2′,5-diacetyl-5-dihydrocoriolin C was dissolved in 1.0 ml dimethylformamide and reacted with 1 ml methyl iodide at the presence of 182 mg silver oxide at 40° C. for 2 hours. The reaction products were subjected to silica gel chromatography to obtain 316 ml oily products of 2′,5-diacetyl-5-dihydro-8-methoxycoriolin C. Yield: 63.8%.

1.3 g of the above compound was dissolved in 100 ml methanol, added with 4.8 ml 2% aqueous solution of sodium hydrogen carbonate and then treated at 57°–60° C. for one hour. The reaction solution was neutralized with 1N hydrochloric acid and concentrated. The concentrated solution was dissolved into a small amount of ethylacetate, washed with water and ethylacetate phase was concentrated and dried. The residues obtained were dissolved in a small amount of chloroform and subjected to chromatography using 30 ml silica gel. They were eluted by chloroform and then 0.5% methanol-chloroform solution, and the eluate was concentrated and dried to obtain 620 mg aimed products in amorphous solid. Yield: 56.83%. NMR $(CDCl_3)$: 3.35 ($-OCH_3$, s)

(3) Synthesis of 1α-(α-hydroxyoctanoyl)-4-(16-carboethoxy-15α-butanolid)-5β-hydroxy-6β,7β-oxide-8-methoxyhirstan 180 mg metal sodium was dissolved in 5 ml absolute ethanol, incorporated with 3 ml diethylmalonate and then kept at 55° C. for 30 minutes. 473 mg 5-dihydro-8-methoxycoriolin C dissolved in 1 ml ethanol was added to the above solution and reacted at 57°–62° C. for two hours. Each 15 ml of ethylacetate and water was added to the above reaction solution, shaked, and ethylacetate phase was isolated and washed with water. The ethylacetate phase was separated and dried under vacuum. The residues were crystallized by addition of a small amount of n-hexane, filtered and dried to obtain 225 mg needle-like crystal. Melting point: 104.5°–105.5° C. Yield: 38.2% NMR $(CDCl_3)^\delta$: 3.25 ($-OCH_3$, s): 4.25 4.00 ($-OCH_2CH_3$, d, J=7).

COMPARISON EXAMPLE 4

Synthesis of 1α(α-hydroxyoctanoyl)-4-(16-carboethoxy-15α-butanolid)-6β,7β-oxide-5β,8β-dihydroxyhirstan

(1) Synthesis of 8-O-tetrahydropyranyl-5-dihydrocoriolin C 1.0 g 2′,5-diacetyl-5-dihydrocoriolin C was dissolved in 20 ml anhydrous benzene, to which 20 mg p-toluene sulfonic acid and 0.37 ml 3,4-dihydro-2H-pyran were added and reacted in the same manner as in the comparison example 2(1). Then, the aimed products were extracted using ethylacetate to obtain 1.35 g oily products of 2′,5-diacetyl-8-0-tetrahydropyranyl-5-dihydrocoriolin C. The products were hydrolyzed using 2% aqueous solution of sodium hydrogen carbonate in methanol to obtain 1.06 g oily products of 8-0-tetrahydropyranyl-5-dihydrocoriolin C.

(2) Synthesis of 1α-(α-hydroxyoctanoyl)-4-(16-carboethoxy-15α-butanolid)-6β,7β-oxide-5β,8β-dihydroxyhirstan 100 mg metal sodium was dissolved in 2 ml absolute ethanol, added with 2 ml diethylmalonate and kept at 55° C. for 30 minutes, to which was added 309 mg 8-0-tetrahydropyranyl-5-dihydrocoriolin C dissolved in 1 ml ethanol. They were reacted at 58° C. for 3 hours. Each 10 ml of ethylacetate and water were added to the above reaction solution, shaked and ethylacetate phase was separated and washed with water.

The solvent phase was concentrated and dried under vacuum and the residues were dissolved in 15 ml methanol, incorporated with 0.03 ml conc.hydrochloric acid and then left at room temperature for one hour. After concentrating the reaction solution, ethylacetate and water were added and the solvent phase was separated, washed with water, concentrated and dried to solid. The residues were crystallized by the treatment with a small amount of n-hexane and the resulted crystal was filtered and dried to obtain 120 mg aimed products as needle-like crystal. Melting Point: 129°–131° C., Yield: 37.5%. NMR $(CDCl_3)^\delta$: 4.18, 3.97 ($-OCH_2CH_3$, d, J=7).

COMPARISON EXAMPLE 5

Synthesis of 1α-octanoyl-4-(16-carbomethoxy-15α-butanolid)-5β-hydroxy-6β,7β-oxide-8β-methoxyhirstan 60 mg metal sodium was dissolved in 1.0 ml absolute methanol. The solution was kept at 47° C. and 0.85 ml dimethylmalonate was added thereto under stirring and they were stirred for further 30 minutes at 47° C. 200 mg 8-methoxycoriolin B was then added to react at 58°–61° C. for 7 hours and then left at room temperature over a night.

The reaction solution was neutralized with 1N-hydrochloric acid and the precipitates deposited were recovered through filtration, washed with aqueous methanol and then dried to obtain 140 mg crude crystal of aimed products.

The coarse crude thus resulted was recrystallied from aqueous methanol to obtain 70 mg needle-like crystal. Melting point: 138°–139° C.

The crystal was again recrystallized from a mixed solution of ethylacetate and n-hexane to obtain 50 mg needle-like crystal of the aimed products. Melting point: 149.5°–151° C. NMR (CDCl$_3$)$^\delta$: 3.25 (—OC$\underline{H}_3$, s): 3.75 (—COOC$\underline{H}_3$, s).

The production process according to this invention is to be described specifically referring to Examples.

EXAMPLE 1

Synthesis of 1α-octanoyl-4-(16-methylene-15α-butanolid)5α-hydroxy-6β,7β-oxide-8β-methoxyhirstan (compound No. 1)

(1) 650 mg 1α-octanoyl-4-(16-carboethoxy-15α-butanolid)-5β-hydroxy-6β,7β-oxide-8β-methoxyhirstan was dissolved in 65 ml methanol and heated under reflux for one hour and 20 minuites with addition of 6.5 ml 1N-sodium hydroxide. The reaction solution was neutralized with 1N-hydrochloric acid and concentrated. Each 20 ml of ethylacetate and water were added to the concentrate. After the solution was shaked, ethylacetate phase was separated and was washed with a small amount of water. The ethylacetate phase was concentrated, dried to solid and recrystallied from a mixed solution of ethylacetate and n-hexane to obtain 635 mg needle-like crystal of 1α-octanoyl-4-(16-carboxy-15α-butanolid)-5β-hydroxy-6β,7β-oxide-8β-methoxyhirstan. Melting point (decomposition point): 178°–179° C.

(2) 635 mg of the compound obtained in (1) above was dissolved in 2.9 ml methanol, to which were added 0.53 ml diethylamine and 0.31 ml 30% aqueous solution of formaldehyde under stirring and reacted at room temperature for 2 hours. The reaction solution was concentrated under vacuum and the residual solution was adjusted with its pH value to 4 by addition of 50 ml ethylacetate, 30 ml water and a proper amount of 1N-hydrochloric acid accompanying shaking. Ethylacetate phase was separated and washed with a small amount of water. The ethylacetate phase was concentrated and 495 mg of the residues were recrystallized from ethylacetate-n-hexane to obtain 160 mg aimed products, that is, compound No. 1. in needle-like crystal. Melting point: 152°–153° C.

NMR (CDCl$_3$)$^\delta$: 3.43 (—OC$\underline{H}_3$, s): 6.23, 5.59 (=C$\underline{H}_2$, s).

Mother liquid separated from the recrystallized products was concentrated, dried to solid and charged to a column filled with 15 ml silica gel, in which they were eluted with chloroform, 0.5% methanol-chloroform and 1% methanol-chloroform successively, and fraction containing aimed products was separated, concentrated and recrystallized to obtain 140 mg secondary crystal. Melting point: 149°–149.5° C. Total yield: 300 mg.

EXAMPLES 2–4

Compounds having the following general formula and listed in the table below were synthesized in the same manner as in Example 1.

| Ex. No. | Compound No. | Aimed substance | Starting substance (amount used) | Reaction (1) (1) MeOH (2) 1N-NaOH (3) Reaction condition | Free acid yield (amount used) | Reaction (2) (1) MeOH (2) 30% HCHO aqueous (3) diethylamine (4) reaction condition | Aimed products (1) output (2) yield | Appearance physical property |
|---|---|---|---|---|---|---|---|---|
| 2 | 2 | R:—CO(CH$_2$)$_6$CH$_3$<br>X:=CH$_2$<br>Z:—OH | R:—CO(CH$_2$)$_6$CH$_3$<br>X:—COOC$_2$H$_5$<br>Z:—OH<br>(600 mg) | (1) 30 ml<br>(2) 2.1 ml<br>(3) reflux for 15 min. | 570 mg<br>(570 mg) | (1) 2.3 ml<br>(2) 0.29 ml<br>(3) 0.46 ml<br>(4) for 1 hr. 50 min. at room temp. | (1) 228 mg<br>(2) 44.1% | needle-like crystal<br>mp : 164.5°~165.5° C.<br>NMR(CDCl$_3$)$^\delta$:<br>5.31, 6.00 (=CH$_2$) |
| 3 | 3 | R:—COCHC$_6$H$_{13}$<br>     \|<br>     OH<br>X:=CH$_2$<br>Z:—OCH$_3$ | R:—COCHC$_6$H$_{13}$<br>     \|<br>     OH<br>X:—COOC$_2$H$_5$<br>Z:—CH$_3$<br>(228 mg) | (1) 6 ml<br>(2) 0.52 ml<br>(3) reflux for 20 min. | 220 mg<br>(220 mg) | (1) 0.9 ml<br>(2) 0.14 ml<br>(3) 0.22 ml<br>(4) for 1 hr. at room temp. | (1) 130 mg<br>(2) 65.6% | amorphous<br>mp: 54°~58° C.<br>NMR(CDCl$_3$)$^\delta$:<br>3.40 (—OCH$_3$, s)<br>5.57, 6.21 (=CH$_2$) |
| 4 | 4 | R:—COCHC$_6$H$_{15}$<br>     \|<br>     OH<br>X:=CH$_2$<br>Z:—OH | R:—COCHC$_6$H$_{13}$<br>     \|<br>     OH<br>X:—COOC$_2$H$_5$<br>Z:—OH<br>(600 mg) | (1) 30 ml<br>(2) 2 ml<br>(3) reflux for 30 min. | 510 mg<br>(510 mg) | (1) 2 ml<br>(2) 0.25 ml<br>(3) 0.4 ml<br>(4) for 2 hr. at room temp. | (1) 200 mg<br>(2) 37.5% | Needle-like crystal<br>mp: 129°~131° C.<br>NMR(CDCl$_3$)$^\delta$:<br>5.35, 6.05 (=CH$_2$) |

EXAMPLE 5

Synthesis of 1α-octanoyl-4-(16-methylene-15α-butanolid)-5-oxo-6β, 7β-oxide-8β-methoxyhirstan (compound No. 5)

200 mg 1α-octanoyl-4-(16-methylene-15α-butanolid)-5β-hydroxy-6β,7β-oxide-8β-methoxyhirstan was dissolved in 5 ml pyridine, to which was added under ice cooling a suspension having been prepared by adding 200 mg chromic acid under ice cooling to 7 ml pyridine. They were reacted while stirred for further 48 hours at 10° C. The reaction solution was filtered and the filtrate was extracted by ethylacetate with addition of water. Ethylacetate phase was isolated, washed with water, concentrated, and then dried. The residues were subjected to chromatography using 10 ml silica gel. The adsorption layer on the silica gel was eluted by chloroform and then 0.7% methanol-chloroform successively and the fraction containing eluate from the 0.7% methanol-chloroform was concentrated dried and recrystallized from ethylacetate-n-hexane to obtain 180 mg aimed products as needle-like crystal. Melting point: 68°–69° C. (89.6% yield) NMR: (CDCl$_3$)$^\delta$: 3.45 (s, OC$\underline{H}_3$); 5.58, 6.17 (=C$\underline{H}_2$).

EXAMPLE 6

Synthesis of
1α-octanoyl-4-(16-methylene-15α-butanolid)-5-oxo-6β,7β-oxide-8β-hydroxyhirstan (Compound No. 6) (1)
Synthesis of 1α-octanoyl-4-(16-methylene-15α-butanolid)-6β,7β-oxide-5β-acetoxy-8β-hydroxyhirstan 700 mg of 1α-octanoyl-4-(16-methylene-15α-butanolid)-6β,7β-oxide-5β,8β-dihydroxyhirstan was dissolved in 3 ml pyridine, added with 0.21 ml acetic anhydride and reacted at 2°–3° C. for 24 hours. The reaction solution was diluted with water and extracted with ethylacetate, and the extract was washed with water and concentrated under vacuum. 870 mg of the resultant residues were subjected to chromatography using 30 ml silica gel, in which the resultant products were eluted with chloroform, 0.5% methanol-chloroform and 1% methanol-chloroform successively. The fraction containing the aimed products was concentrated and dried to obtain 640 mg (82.9% yield) of the aimed compound as amorphous powder. NMR (CDCl$_3$)$^\delta$: 2.13 (—OCOC$\underline{H}_3$, s).

(2) Synthesis of 1α-octanoyl-4-(16-methylene-15α-butanolid)-6β,7β-oxide-5β-acetoxy-8β-tetrahydropyranylhirstan 640 mg 5-acetoxy compound prepared in (1) above was dissolved in 14 ml benzene to which were added under stirring 0.2 ml 3,4-dihydro-2H-pyran and 18 mg p-toluenesulfonic acid and they were reacted at room temperature for 30 hours.

The reaction solution was charged in a separating funnel and the benzene phase was washed with 5 ml water, 2% sodium hydrogen carbonate aqueous solution and 6 ml water successively.

The benzene phase was concentrated and dried, and the residues were dissolved in 50 ml methanol, added with 2% aqueous solution of sodium hydrogen carbonate and kept at 48°–53° C. for two hours. The reaction solution is concentrated and then shaken with addition of a small amount of water and ethylacetate to separate the ethylacetate phase, which was washed with water, concentrated and then dried to obtain 720 mg oily products of 3-O-tetrahydropyranyl compound.

(3) Synthesis of 1α-octanoyl-4-(16-methylene-15α-butanolid)-5-oxo-6β,7β-oxide-8β-hydroxyhirstan 720 ml 8-O-tetrahydropyranyl compound prepared as in (2) above was dissolved in 7 ml pyridine, to which was added under ice cooling a suspension having been prepared by adding 500 mg chromic acid under ice cooling to 8.5 ml pyridine and they were kept at 20° C. for further 24 hours. The reaction solution was filtered and the filtrate was extracted by the ethylacetate with addition of water.

Ethylacetate phase was separated, washed with water, concentrated and dried.

The residues were dissolved in 16 ml methanol, added with 0.08 ml conc. hydrochloric acid and left at room temperature for two hours during which tetrahydropyranyl groups were removed.

The reaction solution was extracted by ethylacetate with addition of water and the extract was washed with water, concentrated and dried. The residues were subjected to chromatography using 25 ml silica gel in which the adsorption layer on the silica gel was eluted by chloroform and then 1% methanol-chloroform successively and the fraction eluated with 1% methanol-chloroform was concentrated, dried and then recrystallized from ethylacetate-n-hexane solution to obtain 245 mg aimed products in needle-like crystal. Melting point: 175°–175.5° C. NMR (CDCl$_3$)$^\delta$: 5.40, 6.35 (=C$\underline{H}_2$)

EXAMPLE 9–13

Compounds listed in the table below were synthesized in the same manner as in example 8 (3).

| Ex. No. | Compound No. | Aimed substance | Starting substance (amount used) Pyridine (amount used) | CrO$_3$ amount Pyridine amount | (1) reaction temp. (2) reaction time | Aimed products (1) output (2) yield | Appearance physical property |
|---|---|---|---|---|---|---|---|
| 9 | 7 | R:—COCHC$_6$H$_{13}$<br>    \|<br>   OH<br>X:=CH$_2$<br>Y:=O<br>Z:—OCH$_3$ | R:—COCHC$_6$H$_{13}$<br>    \|<br>   OH<br>X:=CH$_2$<br>Y:OH<br>Z:OCH$_3$<br>(120 mg)<br>[1.2 ml] | 100 mg<br>2.0 ml | 3°~7° C.<br>7 days | 30 mg<br>25.1% | amorphous powder<br>mp 42°~45° C.<br>NMR(CDCl$_3$)$^\delta$:<br>3.43(—OCH$_3$,),<br>5.37, 6.30 (=CH$_2$) |
| 10 | 8 | R:—COCHC$_6$H$_{13}$<br>    \|<br>   OH<br>X:=CH$_2$<br>Y:=O<br>Z:—OH | R:—COCHC$_6$H$_{13}$<br>    \|<br>   OH<br>X:=CH$_2$<br>Y:OH<br>Z:—OH<br>(120 mg) | 100 mg<br>2.0 ml | 3°~7° C.<br>7 days | 40 mg<br>35.5% | needle-like crystal<br>mp 98°~99° C.<br>NMR(CDCl$_3$)$^\delta$:<br>5.42, 6.37 (=CH$_2$) |

-continued

| Ex. No. | Compound No. | Aimed substance | Starting substance (amount used) Pyridine (amount used) | CrO3 amount Pyridine amount | (1) reaction temp. (2) reaction time | Aimed products (1) output (2) yield | Appearance physical property |
|---|---|---|---|---|---|---|---|
| 11 | 9 | R: —CO(CH2)6CH3<br>X: —COOC2H5<br>Y: =O<br>Z: —OCH3 | R: —CO(CH2)6CH3<br>X: —COOC2H5<br>Y: —OH<br>Z: —OCH3<br>(200 mg)<br>[5.0 ml] | 250 mg<br>7.0 ml | 10° C.<br>43 hr. | 171 mg<br>85.8% | needle-like crystal<br>mp 129°~ 130.5° C.<br>NMR(CDCl3)$^\delta$:<br>3.29(—OCH3,s)$^\delta$:<br>4.22, 4.00(OCH2CH3,d,j=7) |
| 12 | 10 | R: —COCHC6H13<br>        \|<br>        OH<br>X: —COOC2H5<br>Y: =O<br>Z: —OCH3 | R: —COCHC6H13<br>        \|<br>        OH<br>X: —COOC2H5<br>Y: —OH<br>Z: —OCH3<br>(120 mg)<br>[1.2 ml] | 100 mg<br>2.0 ml | 3°~ 7° C.<br>7 days | 45 mg<br>37.6% | needle-like crystal<br>mp 138°~ 139° C.<br>NMR(CDCl3)$^\delta$:<br>3.28(—OCH3, s)<br>4.23, 4.02(OCH2CH3,d,J=7) |
| 13 | 11 | R: —CO(CH2)6CH3<br>X: —COOH<br>Y: =O<br>Z: —OCH3 | R: —CO(CH2)6CH3<br>X: —COOH<br>Y: —OH<br>Z: —OCH3<br>(200 mg)<br>[5 ml] | 200 mg<br>5.0 ml | 10° C.<br>25 hr. | 121 mg<br>60.7% | amorphous powder<br>mp 42°~ 45° C.<br>NMR(CDCl3)$^\delta$:<br>3.40(—OCH3, s) |
| 14 | 12 | R: —CO(CH2)6CH3<br>X: —COOCH2<br>Y: =O<br>Z: —OCH3 | R: —CO(CH2)6CH3<br>X: —COOCH3<br>Y: —OH<br>Z: —OCH3<br>(55 mg)<br>[1.5 ml] | 65 mg<br>1.5 ml | 15°~ 23° C.<br>19 hr. | 45 mg<br>69.4% | needle-like crystal<br>mp 107°~ 109° C.<br>NMR(CDCl3)$^\delta$:<br>3.30(—OCH3, s)<br>3.70(—COOCH3, s) |

What is claimed is:

1. Coriolin derivatives represented by the general formula:

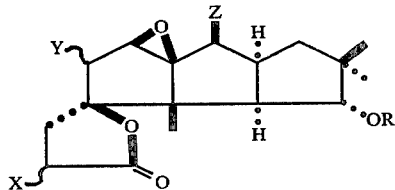

where
R: —CO(CH2)6CH3 or —COCH(OH)(CH2)5CH3,
X: =CH2,
Y: =OH, =O and
Z: —OH or —OCH3.

2. 1α-octanoyl-4-(16-methylene-15α-butanolid)-5-oxo-6β,7β-oxide-8β-methoxyhirstan.

3. 1α-octanoyl-4-(16-methylene-15α-butanolid)5-oxo-6β,7β-oxide-8β-hydroxyhirstan.

4. 1α-(α-hydroxyoctanoyl)-4-(16-methylene-15α-butanolid)-5-oxo-6β,7β-oxide-8β-methoxyhirstan.

5. 1α-(α-hydroxyoctanoyl)-4-(16-methylene-15α-butanolid)-5-oxo-6β,7β-oxide-8β-hydroxyhirstan.

* * * * *